United States Patent [19]

Bolhofer

[11] 4,241,072

[45] Dec. 23, 1980

[54] SUBSTITUTED UREAS AND PROCESSES FOR THEIR PREPARATION

[75] Inventor: William A. Bolhofer, Frederick, Pa.

[73] Assignee: Merck & Co., Inc., Rahway, N.J.

[21] Appl. No.: 4,252

[22] Filed: Jan. 18, 1979

[51] Int. Cl.³ .................. A61K 31/425; C07D 277/46
[52] U.S. Cl. .................................... 424/270; 424/251; 424/263; 424/272; 424/273 R; 424/274; 546/122; 546/309; 548/163; 548/194; 548/222; 548/233; 544/245; 544/301; 544/329
[58] Field of Search ................ 548/301, 194; 546/309; 424/263, 270

[56] References Cited

U.S. PATENT DOCUMENTS

| | | | |
|---|---|---|---|
| 2,042,023 | 5/1936 | Schonhofer et al. | 548/301 X |
| 3,404,152 | 10/1968 | Thiele et al. | 424/263 X |
| 3,864,496 | 2/1977 | Diamond et a. | 424/326 |
| 3,896,233 | 7/1975 | Brenner et al. | 424/248 |
| 3,897,555 | 7/1975 | Loev | 424/263 |

FOREIGN PATENT DOCUMENTS

2651499  5/1977  Fed. Rep. of Germany ........... 424/263

OTHER PUBLICATIONS

Bolhofer et al., Chem. Abstracts, vol. 87, abst. No. 102, 178c (1977).
Burger, Medicinal Chemistry, 2nd Ed., frontispage and pp. 79-81, Interscience Publishers, Inc., NY (1960).

*Primary Examiner*—John D. Randolph
*Attorney, Agent, or Firm*—David L. Rose; Harry E. Westlake

[57] ABSTRACT

Organic chemical compounds based upon the urea molecule are disclosed which have potent gastric secretion inhibitory properties. The urea is substituted with a heterocyclic ring which may be substituted with one or more loweralkyl groups. The urea is also substituted with loweralkyl and a lower-alkylamino loweralkyl group. The compounds have profound effects on the inhibition of gastric secretions in the gastro-intestinal tract, and compositions for such uses are also disclosed.

9 Claims, No Drawings

SUBSTITUTED UREAS AND PROCESSES FOR THEIR PREPARATION

BACKGROUND OF THE INVENTION

Excess secretion of gastric acid can cause indigestion and stomach distress and, if prolonged, can result in ulcer formation. Treatment of excess secretion of gastric acid has heretofore consisted mainly of a bland diet, abstinence from certain foods and the use of antacids to neutralize the gastric acid after it is secreted into the stomach. An improved method of treatment would result from the inhibition of gastric acid secretion. it is thus an object of the present invention to provide compounds which inhibit gastric acid secretion. Another object is to provide methods for the preparation of these compounds. A further object is to provide pharmaceutical formulations for the administration of these compounds. Still another object is to provide a method to inhibit gastric secretion. These and other objects of the present invention will become apparent from the following description.

DESCRIPTION OF THE INVENTION

The compounds of the instant invention are best described by reference to the following structural formula:

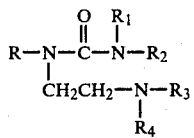

wherein
R is a heterocyclic ring, specifically a 5-membered heterocyclic ring with one or two heteroatoms selected from oxygen, nitrogen or sulfur; a 6-membered non-aromatic heterocyclic ring with one nitrogen heteroatom and wherein said heterocyclic rings may be fused to a benzo or pyridyl moiety, and also wherein said heterocyclic rings may be substituted with one, two or three loweralkyl groups;

$R_1$, $R_2$, $R_3$ and $R_4$ independently are lower-alkyl.

Examples of the 5-membered heterocyclic rings of this invention are thiazole, thiazoline, oxazole, isoxazole, pyrrole, pyrroline, imidazole, imidazoline and the like.

Examples of the 6-membered heterocyclic rings of this invention are dihydropyridine, tetrahydropyridine, tetrahydropyrimidine and the like.

Exemplary fused ring systems are naphthyridine, benzimidazole, benzothiazole, benzoxazole, and the like.

In the above structural formula the lower-alkyl groups may be any alkyl group, straight or branched chain containing from 1 to 6 carbon atoms. Exemplary of such groups are methyl, ethyl, propyl, isopropyl, butyl, tert-butyl, pentyl, hexyl, and the like.

Preferred compounds are realized when the above heterocycles are either unsubstituted or substituted with one or two methyl groups.

Further preferred compounds are realized when $R_1$ and $R_2$ are the same and $R_3$ and $R_4$ are the same and such groups are independently, methyl, ethyl or isopropyl. It's most preferred to have $R_1$, $R_2$, $R_3$ and $R_4$ all as methyl.

The most preferred heterocyclic groups are: thiazole, imidazole, isoxazole and tetrahydropyridine.

The compounds of this invention are prepared in a series of reactions which are outlined in the following reaction sequence:

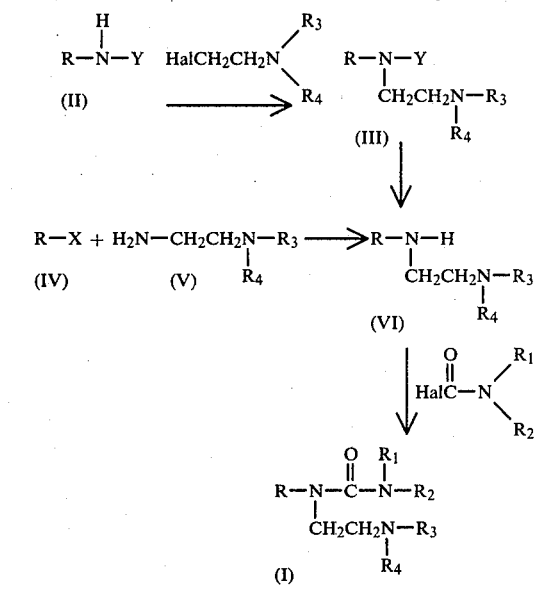

wherein R, $R_1$, $R_2$, $R_3$ and $R_4$ are as above defined, X is a leaving group as defined below, and Hal is a halogen.

The instant compounds (I) are prepared using either of two processes which utilizes the common alkylene diamine intermediate (VI) or by a process which involves alkylation of the urea intermediate VII.

In the first process the alkylene diamine intermediate (VI) is made from the appropriately substituted heterocyclic amine wherein the amine function has been activated by an acyl group (Y). The reaction is carried out in the presence of a strong base such as sodium hydride, lithium hydride, butyl lithium, lithium diisopropylamide and the like, in an appropriate, non-reactive solvent such as dimethylformamide, toluene, dioxane, and the like. The reaction temperature may be in the range of $-70°$ to about 160° C. It is preferred, however, that the reaction temperature be maintained at from about 0° to 100° C.

The activating group (Y) is preferably an acetyl group which is readily bonded to the amino group and which may be selectively removed therefrom.

The activating group is removed hydrolytically with acidic (such as aqueous mineral acid) or basic (such as alkali hydroxide) reagents, under conditions known to those skilled in this art.

Alternatively the ethylene diamine intermediate (VI) is prepared from an appropriate heterocyclic compound (IV) which is substituted with a leaving group X. The leaving group is displaced by the unsubstituted amino group of an appropriately substituted alkylene diamine (V). Suitable leaving groups are halogen, loweralkoxy, loweralkylamino, loweralkylsulfonyl, toluene sulfonyl and the like.

The reaction is carried out generally in the absence of a solvent at temperatures of from about 50° to 150° C. at from 2 hours to as much as one week for difficult reactions. If a solvent is employed it must have a sufficiently high boiling point to allow the reaction to satisfactorily progress to completion. Dimethylformamide, toluene and xylene are exemplary. Generally the reactions are complete in from about 10 hours to 3 days. For those reactions requiring a prolonged heating period, a catalyst, cuprous chloride, may be employed. The use of catalytic amounts of such catalyst will generally reduce the reaction time to within the preferred range. The products are isolated using techniques known to those skilled in this art.

In the final step of the reaction sequence, the compounds of the present invention (I) are prepared by reacting the appropriately substituted alkylene diamine intermediate (VI) with an appropriately substituted carbamoyl halide. The reaction is generally carried out in an inert solvent, preferably an aromatic solvent such as benzene or toluene at a temperature of from about 20° to 120° C., preferably from about 75° to 100° C. Where the reaction temperature exceeds the boiling point of the reaction solution, the reaction is carried out under pressure. It is preferred to contain in the reaction mixture a scavenger for the hydrohalic acid liberated during the course of the reaction. Non-reactive bases, either inorganic or organic may be employed such as triethylamine, pyridine, sodium carbonate, and the like. The base is required in a single molar equivalent to the acid being liberated, however, excess base has not been found to be detrimental. The product (I) is isolated and purified as the free base or acid addition salt using known techniques. The halogen Hal may be any halogen, however, it is preferred to use chlorine.

Optionally the alkylene diamine intermediate (VI) may be converted into an anion before it is reacted with the carbamoylhalide. Reactive alkali metal compounds such as sodium hydride, butyl lithium and the like may be employed. The diamine and the alkali metal compound are combined preferably at room temperature in the foregoing inert solvent in equivalent amounts. If this method is employed the acid scavenger is not needed since an alkali metal halide is the reaction by-product.

An alternative process for the preparation of compounds of formula I is to react a compound of formula VII with a dialkylaminoethyl halide, to give a compound of formula I under conditions similar to those described for the process wherein a compound of formula III is prepared by reacting a dialkylaminoalkyl halide with a compound of formula II. The compounds of formula VII may be prepared by reacting a heterocyclic amine($RNH_2$) with an appropriately substituted carbamoyl halide in the presence of a strong base, such as sodium hydride or lithium hydride in an inert solvent. Alternatively, the compound of formula VII can be prepared by reacting an N-heterocyclic urethane, VIII, with an appropriately substituted diloweralkylamine in a pressure vessel. The reaction is carried out in a solvent preferably a loweralcohol, with excess diloweralkylamine, at from about 90°–120° C. for from 1-3 days.

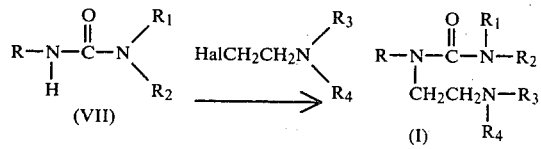

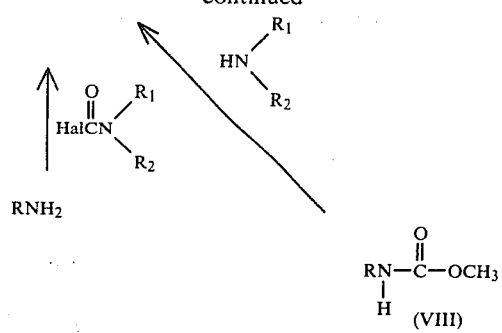

During the course of these processes, the replacement of labile hydrogen atoms attached to heterocyclic ring nitrogen atoms may be necessary to prevent unwanted side reactions with reagents utilized for intermediate or product synthesis. The masking or protective effect is achieved with a group that is itself inert to subsequent reaction conditions but is capable of being removed by cleavage reactions, which leave the remainder of the structure unaffected. The benzyl group has been used for this purpose. It is incorporated on the heterocyclic nitrogen atom under basic alkylating conditions using a benzyl halide such as benzyl chloride as the alkylating agent. Removal of the benzyl group is accomplished by reductive debenzylation usually by catalytic hydrogenation using platinum or palladium catalysts. Loweralcohols are the preferred solvents and the reaction is carried out substantially at room temperature and is complete in from about 10 to 50 hours.

The compounds of this invention may be isolated and used as the free base or as a pharmaceutically acceptable acid addition salt. Such salts are formed by reaction of the free base with the desired inorganic or organic acid. The salts are prepared using methods known to those skilled in this art. Exemplary inorganic acids are hydrohalic acids such as hydrochloric or hydrobromic, or other mineral acids such as sulfuric, nitric, phosphoric, and the like. Suitable organic acids are maleic, fumaric, tartaric, citric, acetic, benzoic, succinic, isethionic and the like.

The compounds of the present invention in the described dosages may be administered orally, however, other routes such as intra peritoneal, subcutaneous, intramuscular or intravenous may be employed.

The active compounds of the present invention are orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suppositories, suspensions, syrups, wafers, chewing gum, and the like. The amount of active compound in such therapeutically useful compositions or preparations is such that a suitable dosage will be obtained.

The tablets, troches, pill, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type, a liquid carrier such as a fatty oil. Various other materials may be present as coatings or to otherwise modify the physical form of the dosage unit, for instance, tablets, pills or capsules may be coated with shellac, sugar or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amount employed.

When used in the above formulation, the instant compounds are employed at dosages sufficient to suppress gastric acid secretions. The dosages may be given a single daily dose or in divided dosages throughout the day. The specific dose given to a patient will vary with the severity of the condition, the weight of the patient and the particular compound being employed. As such, dosages of from about 5 to 200 mg./kg. have been found to be effective, administered from 1 to 4 times per day.

EXAMPLE 1

N,N-dimethyl-N'-(2-dimethylaminoethyl)-N'-(4-methyl-2-thiazolyl)urea Hydrochloride

A.
N-(4-methyl-2-thiazolyl)-N-(2-dimethylaminoethyl-)acetamide

The reaction is run under a nitrogen atmosphere. To a stirred solution of 31.2 g. (0.20 mole) of 2-acetamido-4-methylthiazole in 300 ml. of DMF is added 9.6 g. (0.20 mole) of a 50% suspension of sodium hydride in mineral oil. The reaction is stirred for ½ hour as the temperature spontaneously rises to 50° C. The reaction is cooled to 35° to 40° C. and a further 12.0 g. (0.25 mole) of sodium hydride suspension added followed by 36.0 g. (0.25 mole) of 2-dimethylaminoethyl chloride HCl, added portionwise for 10 to 15 minutes. The mixture is stirred at room temperature for about 1 hour and then at steam bath temperature for 20 hours. The tan mixture is cooled to ambient temperature and filtered to remove salts. The filtrate is concentrated under reduced pressure at steam bath temperature. This gives 46.4 g. of crude product as a brown oil (containing mineral oil (10.8 g.).

B.
N,N-dimethyl-N'-(4-methyl-2-thiazolyl)-1,2-ethanediamine

To the crude product from Part A is added 200 ml. of 6 N hydrochloric acid. The solution is stirred at reflux for 20 hours. The reaction mixture is cooled in ice and washed by extracting with 100 ml. of ether. The cold acid layer is poured into excess cold 10 N sodium hydroxide with stirring. The aqueous layer is twice extracted with 100 ml. of ether and 100 ml. of methylene chloride. The combined extracts are washed 3 times with 50 ml. of saturated sodium chloride solution, dried over anhydrous sodium sulfate, filtered and concentrated in vacuo affording 32.5 g. of crude dark liquid. This is distilled in vacuo and 19.0 g. of N,N-dimethyl-N'-(4-methyl-2-thiazolyl)-1,2-ethanediamine with b.p. of 102°–104° C. at 0.5 mm. is obtained.

C.
N,N-dimethyl-N'-(2-dimethylaminoethyl)-N'-(4-methyl-2-thiazolyl)urea Hydrochloride To a stirred solution of 12.95 g. (0.07 mole) of N,N-dimethyl-N'-(4-methyl-2-thiazolyl)-1,2-ethanediamine in 100 ml. of dry benzene is added 9.1 g. (0.055 mole) of dimethylcarbamoyl chloride and 8.6 g. (0.085 mole) of triethylamine. The mixture is stirred at reflux for 6 hours and overnight at room temperature. 100 Ml. of ether is added, the mixture is filtered and concentration of the filtrate in vacuo gives 19.3 g. of amber oil. The oil is dissolved in 5 ml. of cold ethanol, cooled in ice and treated with 10.5 ml. (0.063 mole) of 6 N ethanolic hydrochloric acid. Dilution with excess ether gives 17.3 g. of a yellow solid, m.p. 126°–132° C. Recrystallization from ethanol and ether affords 12.9 g. of N,N-dimethyl-N'-(2-dimethylaminoethyl)-N'-(4-methyl-2-thiazolyl-)urea hydrochloride with m.p. of 130°–133° C.

EXAMPLE 2

N,N-dimethyl-N'-(2-dimethylaminoethyl)-N'-(5-methyl-3-isoxazolyl)urea Hydrochloride

A.
N-(2-dimethylaminoethyl)-N-(5-methyl-3-isoxazolyl-)acetamide

The reaction is run under a nitrogen atmosphere. To a stirred solution of 14.0 g. (0.10 mole) of N-(5-methyl-3-isoxazolyl)acetamide in 100 ml. of dry dimethyl formamide is added 4.3 g. (0.10 ml.) of the 56% sodium hydride suspension. An immediate reaction occurs and solids begin to separate (temperature rises to 55° C.). Then 15.8 g. (0.11 mole) of 2-dimethylaminoethyl chloride hydrochloride is added portionwise along with an additional 4.3 g. (0.11 mole) of sodium hydride (temperature rises to 75°–85° C.). The mixture is stirred for 15 minutes until the temperature begins to fall and is then heated on the steam bath for 28 hours. The dark mixture is filtered to remove precipitated salts, and the dark filtrate is concentrated under reduced pressure at 80°–90° C. This affords 21.7 g. of dark liquid which is dissolved in 150 ml. of ether, filtered through charcoal and concentrated to give 19.0 g. of pale yellow liquid which is used as is in the next step.

B.
N,-dimethyl-N'-(5-methyl-3-isoxazolyl)-1,2-ethanediamine

A solution of 19.0 g. (0.09 mole) of N-(2-dimethylaminoethyl)-N-(5-methyl-3-isoxazolyl)acetamide in 100 ml. of 3 N hydrochloric acid is stirred at steam bath temperature for 3 hours. The reaction mixture is cooled to room temperature and washed with ether. Concentration of the hydrochloric acid solution in vacuo gives a viscous amber oil which is neutralized with saturated sodium carbonate solution using some solid sodium carbonate. The aqueous layer is extracted with 100 ml. of methylene chloride. The organic layer is dried over anhydrous sodium carbonate, filtered and concentrated in vacuo. This gives 10.2 g. of amber waxy solid identified by NMR as N,N-dimethyl-N'-(5-methyl-3-isoxazolyl)-1,2-ethane-diamine.

C.
N,N-dimethyl-N'-(2-dimethylaminoethyl)-N'-(5-methyl-3-isoxazolyl)urea Hydrochloride To a stirred solution of 8.46 g. (0.05 mole) of N,N-dimethyl-N'-(5-methyl-3-isoxazolyl)-1,2-ethane-diamine in 75 ml. of benzene (dry) is added 5.6 g. (0.055 mole) of triethylamine followed by 5.9 g. (0.055 mole) of dimethylcarbamoyl chloride. The solution is slowly heated to 85° C. and stirred at 80°–85° C. for 6 hours. The reaction mixture is filtered and the filtrate is concentrated in vacuo. The reddish liquid residue is taken up in 125 ml. of hexane and filtered through charcoal which is then washed well with ether. Concentration of the combined filtrates in vacuo gives 10.3 g. of a reddish liquid. This is dissolved in 5 ml. of ethanol, cooled in ice and 6.8 ml. of 6 N ethanolic hydrochloric acid is added. Addition of ether precipitates the mono hydrochloride salt (11.5 g.) as an "off white" solid, which is filtered and dried in vacuo. The salt is recrystallized by dissolving it in 15 ml. of hot ethanol, adding ether with stirring to incipient cloudiness (35–40 ml.), and slowly diluting with another 100–110 ml. of ether when crystallization is well underway. Filtration affords 9.9 g. of white solid, m.p. 142.5°–143.5° C.

EXAMPLE 3
N,N-Dimethyl-N'-(2-dimethylaminoethyl)N'-(1-methyl-2-imidazolyl)urea Dihydrobromide

A.
N,N-Dimethyl-N'-(1-methyl-2-imidazolyl)-1,2-ethanediamine

Dissolve 9.5 g. (0.0683 moles) of N-(1-methyl-2-imidazolyl)acetamide in 150 ml. of dimethylformamide under nitrogen. 3.375 g. (0.75 moles) of sodium hydride 50% suspension is added and stirred at 30°–40° C. until gas evolution ceases. The reaction mixture is cooled to room temperature and an additional 3.375 g. of sodium hydride added along with 10.8 g. (0.075 moles) of dimethylaminoethyl chloride hydrochloride. The reaction mixture is stirred at 30°–45° C. until gas evolution ceases and at 50° C. for ½ hour and at 90° C. for 2 hours. The mixture is cooled to room temperature, 20 ml. of ethanol added and the mixture evaporated in vacuo. The residue is taken up in 150 ml. of 6 N hydrochloric acid and refluxed for 24 hours. The aqueous acid layer is extracted with hexane and then neutralized with 50 ml. of saturated sodium carbonate. The aqueous layer is extracted with chloroform (100 ml., 10 times) the organic layer washed with saturated sodium chloride, and evaporated to dryness affording 8.8 g. of oil identified as N,N-dimethyl-N'-(1-methyl-2-imidaziolyl)-1,2-ethanediamine, which is used as in the next step.

B.
N,N-Dimethyl-N'-(2-dimethylaminoethyl)-N'-(1-methyl-2-imidazolyl)urea Dihydrobromide In 125 ml. of dry benzene is dissolved 8.6 g. (0.0512 moles) of the product of Part A, 6 g. (0.06 moles) of triethylamine and 6.0 g. (0.056 moles) of dimethylcarbamoylchloride. The reaction mixture is stirred at room temperature for 15 minutes and refluxed overnight. The reaction is diluted with 5 ml. of ethanol and 125 ml. of ether, filtered and the filtrate is evaporated to dryness. The residual oil is chromatographed on 300 g. of silica gel and eluted with a solvent mixture of 100 ml. of chloroform, 200 ml. of isopropanol, and 50 ml. of triethylamine. The combined product fractions are dissolved in ether and saturated with hydrogen bromide gas. The collected precipitate is recrystallized from ethanol to give 5.5 g. of N,N-dimethyl-N'-(2-dimethylaminoethyl)-N'-(1-methyl-2-imidazolyl)urea dihydrobromide m.p. 187.5°–189.5° C.

EXAMPLE 4
N,N-Dimethyl-N'-(2-dimethylaminoethyl)-N'-(4,5-dimethyl-2-thiazolyl)urea Dihydrochloride

A.
N,N-Dimethyl-N'(4,5-dimethyl-2-thiazolyl)-1,2-ethane diamine

Dissolve 30.0 g. (0.176 moles) of N-(4,5-dimethyl-2-thiazolyl) acetamide in 375 ml. of dimethylformamide under nitrogen followed by 7.7 g. of 50% sodium hydride in 2 portions at room temperature. When gas evolution ceases, 27.5 g. (0.191 moles) of dimethylaminoethylchloride hydrochloride is added along with 8.35 g. of 50% sodium hydride. The mixture is stirred at 60°–70° C. for ½ hour, 90° C. for 2 hours, cooled to room temperature, and concentrated in vacuo. The residue is taken up in 200 ml. of 6 N hydrochloric acid and refluxed for 24 hours. The mixture is extracted with hexane and made basic with sodium hydroxide with cooling. The aqueous layer is extracted with methylene chloride, the organic layer washed with saturated sodium chloride, dried over sodium sulfate and evaporated. The residue is distilled and the fraction boiling at 110°–113° C./0.7 mm. of Hg. collected (29.2 g.) and identified as N,N-dimethyl-N'-(4,5-dimethyl-2-thiazolyl)-1,2-ethanediamine.

B.
N,N-Dimethyl-N'-(2-dimethylaminoethyl)-N'-(4,5-dimethyl-2-thiazolyl)urea Dihydrochloride Following the reaction procedure of Example 3B using 13 g. (0.0653 moles) of the product of Example 4A, 7.7 g. (0.076 moles) of triethylamine, 7.65 g. (0.071 moles) of dimethylcarbamoylchloride in 135 ml. of dry benzene and adding ethanolic hydrogen chloride to the product oil, there is obtained 19 g. of N,N-dimethyl-N'-(2-dimethylaminoethyl)-N'-(4,5-dimethyl-2-thiazolyl)urea dihydrochloride, m.p. 123°–128° C.

EXAMPLE 5
N,N-Dimethyl-N'-(2-dimethylaminoethyl)-N'-[5,7-dimethyl-2-(1,8-naphthyridyl)]urea Dihydrochloride

A.
2-(2-Dimethylaminoethylamino)-5,7-dimethyl-1,8-naphthyridine

A mixture of 5.7 g. (0.0296 moles) of 2-chloro-5,7-dimethyl-1,8-naphthyridine and 6.6 ml. (0.062 mole) N,N-dimethylethylene diamine is heated at 105° C. for 1½ hours. The reaction is cooled, dissolved in water, neutralized within sodium hydroxide, the product extracted into methylene chloride, dried, filtered through charcoal and evaporated affording 8.6 gm. of 2-(2-dimethylaminoethylamino)-5,7-dimethyl-1,8-naphthyridine.

B.
N,N-Dimethyl-N'-(2-dimethylaminoethyl)-N'-[5,7-dimethyl-2-(1,8-naphthyridyl)]urea Dihydrochloride To a solution of 10.5 gm. (0.043 moles) of 2-(2-dimethylaminoethylamino)-5,7-dimethyl-1,8-naphthyridine in 50 ml. dry benzene is added 4.0 ml. (0.043 moles) of dimethylcarbamoyl chloride and 6.2 ml. (0.044 moles) of triethylamine and it is then refluxed for 2 hours. Working up the reaction as in Example 3B, adding ethanolic hydrogen chloride to the product oil, and recrystallizing from isopropanol affords 5.5 g. of N,N-dimethyl-N'-(2-dimethylaminoethyl)-N'-[5,7-dimethyl-2-(1,8-naphthyridyl)]urea dihydrochloride m.p. 217°–218° C.

EXAMPLE 6

N,N-Dimethyl-N'-(2-dimethylaminoethyl)-N'-(4,4,6-trimethyl-3,4-dihydro-2-pyridyl)urea Dihydrobromide

A. Ethyl 3-methylamino-3-iminopropionate Hydrochloride

To a solution of 7.0 gm. (0.22 mole) of methylamine dissolved in 50 ml. of absolute ethanol at ice-bath temperature is added 41.4 gm. (0.207 mole) of ethyl ethoxycarbonylacetimidate hydrochloride. The reaction mixture is allowed to warm to room temperature and stirred for 5 hours. The solvent is removed and a mixture of acetone-ether is added to induce crystallization. 36.8 Gm. of crystalline product is collected as the hydrochloride salt.

B. 2-Methylamino 4,4,6-Trimethyl-3,4-dihydropyridine

To a solution of 9.0 gm. (0.05 mole) of ethyl 3-methylamino-3-iminopropionate hydrochloride in 50 ml. of absolute ethanol is added 3.4 gm. (0.05 mole) of sodium ethoxide followed by a solution of 4.9 gm. (0.05 mole) of mesityloxide in 25 ml. of absolute ethanol. The mixture is refluxed overnight. The salts are filtered while the solution is still hot and the filtrate evaporated. The residue is diluted with methylcyclohexane and evaporated to a semi-solid, diluted with ether, cooled and filtered affording 1.9 gm. of 2-methylamino 4,4,6-trimethyl-3,4-dihydropyridine m.p. 122°–124° C.

C. 2-Methylamino-4,4,6-trimethyl-3,4-dihydropyridine

A mixture of 4.0 g. (0.024 mole) of (2-methylamino 4,4,6-trimethyl, 3,4-dihydropyridine and 5.9 ml. (0.055 mole) of N,N-dimethyl ethylene diamine is heated at 100° C. for 2 hours. The excess diamine is removed under vacuum affording 5.7 gm. of the title compound as an oil which is used as in the next step.

D. N,N-Dimethyl-N'-(2-dimethylaminoethyl)-N'-(4,4,6-trimethyl-3,4-dihydro-2-pyridyl)urea Dihydrobromide Monohydrate A solution of 5.7 gm. (0.027 mole) of crude 2-methylamino 4,4,6-trimethyl-3,4-dihydropyridine in 30 ml. of dry benzene containing 2.5 ml. (0.027 mole) of dimethylcarbamoyl chloride and 3.8 ml. (0.027 mole) of triethylamine is heated at reflux for 4 hours. Working up as in Example 1C dissolving the product oil in ether and bubbling in gaseous hydrogenbromide affords 4.0 gm. of N,N-dimethyl-N'-(2-dimethylaminoethyl)-N'-(4,4,6-trimethyl-3,4-dihydro-2-pyridyl)urea dihydrobromide monohydrate m.p. 114°–121° C.

EXAMPLE 7

N,N-Dimethyl-N'-(2-dimethylaminoethyl)-N'-(4,6-dimethyl-3,4,5,6-tetrahydro-2-pyridyl)urea Dihydrobromide

A. 2-(Dimethylaminoethylamino)-4,6-dimethyl-3,4,5,6-tetrahydropyridine

To a solution of 1.32 gm. (0.015 mole) N,N-dimethyl ethylene diamine in 5 ml. of methanol is added 2.5 ml. of 6 N ethanolic hydrochloric acid and 2.1 gm. (0.0149 mole) of 2,3-dimethyl 2,3,4,5-tetrahydro-6-methoxypyridine. The reaction is stirred at room temperature for 23 hours. The solvent is evaporated and the residue dissolved in water. Sodium hydroxide is added and the mixture is extracted into methylene chloride dried and evaporated affording 3.0 g. of 2-(dimethylaminoethylamino)-4,6-dimethyl-3,4,5,6-tetrahydropyridine.

B. N,N-Dimethyl-N'-(2-dimethylaminoethyl)-N'-(4,6-dimethyl-3,4,5,6-tetrahydro-2-pyridyl)urea Dihydrobromide Hydrate To a solution of 8.2 g. (0.041 mole) of 2-(dimethylaminoethylamino)-4,6-dimethyl-3,4,5,6-tetrahydropyridine in 80 ml. of dry toluene is added 2.4 g. (0.05 mole) of 50% sodium hydride. After warming to 70° C. for 1 hour 4.1 ml. (0.044 mole) of dimethylcarbamoyl chloride is added and refluxed for 1½ hours. Water is added, extracted with benzene then extracted in hydrochloric acid, washed with benzene, neutralized the aqueous layer with sodium carbonate and extracted the product into methylene chloride, dried and evaporated to give an oil which is treated with hydrogen bromide gas in ether. The collected precipitate is crystallized from acetone to give 3.3 gm. of N,N-dimethyl-N'-(2-dimethylaminoethyl)-N'-(4,6-dimethyl-3,4,5,6-tetrahydro-2-pyridyl)urea dihydrobromide monohydrate m.p. 136°–138° C.

EXAMPLE 8

N,N-Dimethyl-N'-(2-dimethylaminoethyl)-N'-[2-(1-pyrrolinyl)]urea Dihydrochloride Hydrate

A. 2-(Dimethylaminoethylamino-1-pyrroline

Into a solution of 4.4 gm. (0.05 mole) of N,N-dimethylethylene diamine in 15 ml. of methanol with cooling is added 3.6 gm. (0.1 mole) of hydrogen chloride gas and then at room temperature is added 5.6 gm. (0.05 mole) of 88% 2-methoxy-1-pyrroline and let stir at ambient temperature for 22½ hours. Removed the methanol, dissolved the residue in water, neutralized with sodium hydroxide and extracted with methylene chloride, dried and evaporated affording 8.0 gm. of 2-(dimethylaminoethylamino)-1-pyrroline.

B. N,N-Dimethyl-N'-(2-dimethylaminoethyl)-N'-[2-(1-pyrrolinyl)]urea Dihydrochloride Hydrate Following the procedure of Example 7B using 1.6 g. (0.01 mole) of 2-(dimethylaminoethylamino)-1-pyrroline, 25 ml. of dry toluene, 0.6 g. (0.012 mole) of 50% sodium hydride and 1.0 ml. (0.011 mole) of dimethylcarbamoyl chloride there is obtained, after treatment with ethanolic hydrogen chloride, 1.1 g. of N,N-dimethyl-N'-(2-dimethylaminoethyl)-N'-[2-(1-pyrrolinyl)]urea dihydrochloride hydrate m.p. 210°–213° C.

EXAMPLE 9

N,N-Dimethyl-N'-(2-dimethylaminoethyl)-N'-(2-benzimidazolyl)urea Dihydrobromide

A. N,N-Dimethyl-N'-(2-benzimidazolyl)-1,2-ethane diamine

27.2 G. (0.139 moles) of 2-methanesulfonyl benzimidazole and 26.5 g. (0.3 moles) of N,N-dimethylethylene diamine are combined and heated at 170°–175° C. for 5 hours. The mixture is then cooled and concentrated in vacuo. The residue is dissolved in methylene chloride washed with saturated sodium chloride, dried over sodium sulfate and evaporated to dryness affording 22 g. of N,N-dimethyl-N'-(2-benzimidazolyl)-1,2-ethane diamine compound which is recrystallized from benzene yielding 20.3 g. with a m.p. of 143.5–145.5.

B. N,N-Dimethyl-N'-(2-dimethylaminoethyl)-N'-(2-benzimidazolyl)urea Dihydrobromide

Following the procedure of Example 1C, using 9.4 g. (0.046 moles) of N,N-dimethyl-N'-(2-benzimidazolyl)-1,2-ethane diamine, 6.0 g. (0.06 moles) of triethylamine, 5.7 g. (0.053 moles) of N,N-dimethylcarbamoyl chloride and 150 ml. of benzene, there is obtained N,N-dimethyl-N'-(2-dimethylaminoethyl)-N'-(2-benzimidazolyl) urea, which, after chromatographic separation on 375 g. of silica gel, and elution with a mixture of 500 ml. of chloroform, 100 ml. of isopropanol, 100 ml. of toluene and 10 ml. of triethylamine, affords 9.4 g. of oil. This is treated with hydrogen bromide and recrystallized from ethanol to give 8.2 g. of dihydrobromide salt, m.p. 193°–195° C.

EXAMPLE 10

N,N-Dimethyl-N'-(2-dimethylaminoethyl)-N'-(2-thiazolyl) urea

Following the procedure of Example 1C using 18.2 g. (0.1065 moles) of N,N-dimethyl-N'-(2-thiazolyl)-1,2-ethane diamine, 12.1 g. (0.120 moles) of triethylamine, 12.5 g. (0.116 moles) of dimethylcarbamoyl chloride and 135 ml. of dry benzene, there is obtained 20.1 g. of N,N-dimethyl-N'-(2-dimethylaminoethyl)-N'-(2-thiazolyl) urea as an oil which is distilled at 108°–110° C., at 0.02 mm. of Hg.

EXAMPLE 11

N,N-Dimethyl-N'-(2-diisopropylaminoethyl)-N'-(5(4)-methyl-4(5)-imidazolyl)urea

A. Methyl N-(5(4)-methyl-4(5)-imidazolyl)carbamate

A suspension of 19.5 gm. (0.130 moles) of freshly prepared 4(5)-methyl-5(4)-imidazole carboxyazide is refluxed in methanol (200 ml.) for ten hours. The reaction is cooled, filtered through charcoal and the solvent removed. Trituration with diethyl ether yields crude product (19.1 gm.), m.p. 152°–156° C.

B. Methyl N-(5(4)-methyl-N-benzyl-4(5)-imidazolyl) carbamate

A mixture of 20.5 gm. (0.132 moles) of methyl N-(5(4)-methyl-4(5)-imidazolyl) carbamate and 17.2 gm. (0.136 moles) of benzyl chloride is heated at 110° C. for 1½ hours. The reaction mixture is cooled, and the product dissolved in 10% aqueous hydrochloric acid and washed with methylene chloride. The aqueous layer is then made basic with saturated sodium carbonate solution and extracted with methylene chloride. The organic layer is filtered through charcoal and evaporated to give 20.5 gm. of crude product. This is chromatographed on silica gel (600 gm.) by gradient elution using 1–25% methanol chloroform as eluent and 11.3 gm. of purified product is obtained. Crystallization from methylene chloride-diethyl ether affords 9.3 gm. of product, m.p. 134°–137° C.

C. N,N-Dimethyl-N'-(5(4)-methyl-N-benzyl-4(5)-imidazolyl)urea

A solution of 15.0 gm. (0.061 mole) of methyl N-(5(4)-methyl-N'-benzyl-4(5)-imidazolyl)carbamate in ethanol (140 moles) containing excess dimethylamine (9.0 gm.) is heated in bomb at 100° C. for 48 hours. The reaction is cooled and the solvent evaporated. The blackish residue is dissolved in 10% aqueous hydrochloric acid, filtered through charcoal, and made basic with saturated sodium carbonate. The product is extracted with methylene chloride and the organic layer is dried over anhydrous sodium sulfate, filtered and evaporated. Trituration with diethyl ether yields 8.7 gm. of product, m.p. 168°–170° C.

D. N,N-Dimethyl-N'-(2-diisopropylaminoethyl)-N'-(5(4)-methyl-N-benzyl-4(5)-imidazolyl)urea

A suspension of 0.9 gm. (0.11 moles) of lithium hydride in a solution of 8.5 gm. (0.033 moles) of N,N-dimethyl-N'-(5(4)-methyl-N-benzyl-4(5)-imidazolyl)urea in dry dioxane (70 ml.) is heated at 105° C. for three hours under a nitrogen atmosphere. Then 6.8 gm. (0.034 moles) of diisopropylaminoethyl chloride hydrochloride is added in small portions and heating continued for 24 hours. The reaction mixture is cooled, diluted with methylene chloride and filtered. The filtrate is evaporated, the residue is dissolved in 10% aqueous hydrochloric acid, washed with methylene chloride and filtered through charcoal. The acid layer is made basic with saturated sodium carbonate, extracted with methylene chloride, dried and evaporated (wt.-16.2 gm.). The solids are dissolved in a minimum amount of methylene chloride and diluted with diethyl ether to a point of cloudiness, gummy product is collected and recrystallized to give 3.2 gm. of purified product. The mother liquors (wt.-11.7 gm.) are combined and chromatographed on silica gel (450 gm.) by gradient elution using 1–4% methanol chloroform as eluent, obtaining 4.0 gm. of additional product. Total yield 7.2 gm.

E. N,N-Dimethyl-N'-(2-diisopropylaminoethyl)-N'-(5(4)-methyl-4(5)-imidazolyl)urea

A solution of 7.2 gm. (0.019 moles) of N,N-dimethyl-N'-(2-diisopropylaminoethyl)-N'-(5(4)-methyl-N-benzyl-4(5)-imidazolyl)urea in ethanol (150 ml.) and conc. hydrochloric acid (8.0 ml.) containing 10% Pd/C (4.0 gm.) is hydrogenated in a Parr apparatus for 20 hours. The catalyst is removed by filtration and the filtrate evaporated. The residue is dissolved in water, made basic with saturated sodium carbonate and extracted with methylene chloride. The organic layer is dried and evaporated. NMR reveals that the reaction has not gone to completion. The solid materials are rehydrogenated twice using the above conditions affording 4.5 g. of product. Crystallization from diethyl ether affords 3.1 g. of product, m.p. 111°–113° C.

What is claimed is:

1. A compound having the formula:

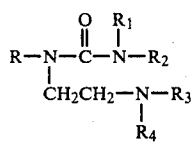

wherein

R is a thiazole which may be substituted with one, or two loweralkyl group; and $R_1$, $R_2$, $R_3$ and $R_4$ are independently loweralkyl and the pharmaceutically acceptable acid addition salts thereof.

2. The compound of claim 1 wherein said thiazole is unsubstituted or substituted with one or two methyl groups.

3. The compounds of claim 1 wherein $R_1$ and $R_2$ are the same and $R_3$ and $R_4$ are the same.

4. The compound of claim 3 wherein $R_1$ and $R_2$ and $R_3$ and $R_4$ are methyl, ethyl or isopropyl.

5. The compound of claim 4 wherein $R_1$, $R_2$, $R_3$ and $R_4$ are all methyl.

6. The compound of claim 5 which is N,N-dimethyl-N'-(2-dimethylaminoethyl)-N'-(4,5-dimethyl-2-thiazolyl)urea.

7. The compound of claim 5 which is N,N-dimethyl-N'-(2-dimethylaminoethyl)-N'-(4-methyl-2-thiazolyl)urea.

8. A method for the inhibition of gastric acid secretions which comprise administering to a subject with excess gastric acid secretions an effective amount of a compound of claim 1.

9. A composition useful for the suppression of gastric acid secretions which comprises an inert carrier and a compound of claim 1.